(12) United States Patent
Seo et al.

(10) Patent No.: US 10,430,940 B2
(45) Date of Patent: Oct. 1, 2019

(54) INSPECTION SYSTEM AND INSPECTION METHOD

(71) Applicant: KOH YOUNG TECHNOLOGY INC., Seoul (KR)

(72) Inventors: Seung Ae Seo, Hwaseong-si (KR); Won Mi Ahn, Goyang-si (KR); Hye In Lee, Gwangmyeong-si (KR); Jong Hui Lee, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 66 days.

(21) Appl. No.: 15/745,495

(22) PCT Filed: Jul. 18, 2016

(86) PCT No.: PCT/KR2016/007813
§ 371 (c)(1),
(2) Date: Jan. 17, 2018

(87) PCT Pub. No.: WO2017/014518
PCT Pub. Date: Jan. 26, 2017

(65) Prior Publication Data
US 2018/0357755 A1    Dec. 13, 2018

(30) Foreign Application Priority Data
Jul. 17, 2015 (KR) .......................... 10-2015-0101735

(51) Int. Cl.
*G06T 7/00* (2017.01)
*G01B 11/02* (2006.01)
(Continued)

(52) U.S. Cl.
CPC .............. *G06T 7/001* (2013.01); *G01B 11/02* (2013.01); *G01B 11/0608* (2013.01);
(Continued)

(58) Field of Classification Search
CPC ......... G06T 7/001; G06T 7/62; G06T 7/0004; G06T 2207/30108; G06T 2207/10052;
(Continued)

(56) References Cited

U.S. PATENT DOCUMENTS

| 2003/0001117 A1* | 1/2003 | Hyun ..................... G01B 11/00 250/559.19 |
| 2003/0062487 A1* | 4/2003 | Hiroi ..................... G01N 23/22 250/492.2 |

(Continued)

FOREIGN PATENT DOCUMENTS

| JP | 2006-267018 | 10/2006 |
| JP | 2013-117414 | 6/2013 |

(Continued)

OTHER PUBLICATIONS

Supplementary European Search Report for European Application No. EP 16 82 8022, dated Apr. 20, 2018.
(Continued)

*Primary Examiner* — Phuoc Tran
(74) *Attorney, Agent, or Firm* — Kile Park Reed & Houtteman PLLC

(57) ABSTRACT

Disclosed are an inspection system and an inspection method of performing image processing on an outline of an inspection object according to whether the inspection object is good or defective, and overlapping and displaying the image-processed outline with reference information for determining whether the inspection object is good or defective. The inspection system includes: a data acquisition unit configured acquire an image of an inspection object by irradiate light on the inspection object; a processing unit configured to detect an outline of the inspection object based on the image data of the inspection object; and an output unit configured to overlap and display the outline with reference information, wherein the processing unit is configured to
(Continued)

determine whether the outline is good or defective based on the reference information to perform image processing on the outline according to whether the outline is good or defective.

11 Claims, 13 Drawing Sheets

(51) Int. Cl.

| | |
|---|---|
| *G01B 11/25* | (2006.01) |
| *G01B 11/06* | (2006.01) |
| *G01N 21/956* | (2006.01) |
| *H05K 1/02* | (2006.01) |
| *H05K 3/34* | (2006.01) |
| *G06T 7/62* | (2017.01) |
| *G01N 21/88* | (2006.01) |
| *G05B 19/418* | (2006.01) |

(52) U.S. Cl.
CPC .......... *G01B 11/25* (2013.01); *G01B 11/2527* (2013.01); *G01N 21/8851* (2013.01); *G01N 21/95684* (2013.01); *G05B 19/41875* (2013.01); *G06T 7/0004* (2013.01); *G06T 7/62* (2017.01); *H05K 1/0269* (2013.01); *H05K 3/3478* (2013.01); *G01N 2021/8887* (2013.01); *G01N 2021/95615* (2013.01); *G01N 2021/95646* (2013.01); *G06T 2207/10052* (2013.01); *G06T 2207/30108* (2013.01); *G06T 2207/30152* (2013.01); *H05K 2203/163* (2013.01)

(58) Field of Classification Search
CPC ......... G05B 19/41875; G01N 21/8851; G01N 21/95684; G01N 2021/8887; H05K 3/3478; H05K 1/0269; G01B 11/2527; G01B 11/25; G01B 11/02
See application file for complete search history.

(56) References Cited

U.S. PATENT DOCUMENTS

| | | |
|---|---|---|
| 2004/0184648 A1 | 9/2004 | Zhang et al. |
| 2013/0182942 A1 | 7/2013 | Fujii et al. |
| 2014/0132953 A1 | 5/2014 | Jeong |
| 2016/0224718 A1 | 8/2016 | Jeong |
| 2016/0231784 A1 | 8/2016 | Yu et al. |

FOREIGN PATENT DOCUMENTS

| | | |
|---|---|---|
| JP | 2014-109493 | 6/2014 |
| KR | 10-0644024 | 11/2006 |
| KR | 10-0890390 | 3/2009 |
| KR | 10-1438157 | 9/2014 |
| KR | 10-1457040 | 10/2014 |
| WO | 2012/098697 | 7/2012 |

OTHER PUBLICATIONS

International Search Report for International Application No. PCT/KR2016/007813, dated Oct. 21, 2016.
Written Opinion for International Application No. PCT/KR2016/007813 with English translations, dated Oct. 21, 2016.

\* cited by examiner

INSPECTION SYSTEM AND INSPECTION METHOD

TECHNICAL FIELD

The present disclosure relates to the inspection field, and more particularly, to an inspection system and a method of inspecting whether an inspection object is good or defective.

BACKGROUND ART

In recent years, as consumer standards for product quality have increased day by day, manufacturers are making efforts to eliminate defective products during production processes, assembly processes, intermediate processes, and final assembly completion processes in producing their products. In order to eliminate defective products, various inspection systems have been used to inspect whether the corresponding products are good (GOOD or PASS) or defective (NG).

Generally, an inspection system irradiates a product, that is, an inspection object, with patterned light generated by a projection unit, and receives light reflected from the inspection object in an imaging unit to acquire an image of the inspection object. In addition, the inspection system performs inspection on the image of the inspection object according to predetermined reference information to determine whether the inspection object is good or defective.

SUMMARY

Conventionally, inspection results for an inspection object have been simply displayed as good or defective through an output unit of an inspection system. As a result, there was a problem in that it was difficult for a user to easily determine what reference information was accountable for an inspection object being determined to be good or defective, only through the inspection results (that is, good or defective) displayed on the output unit.

The present disclosure provides an inspection system and an inspection method of performing image processing on an outline of an inspection object according to whether the inspection object is good or defective, and overlapping and displaying the image-processed outline with reference information for determining whether the inspection object is good or defective.

An inspection system according to an embodiment includes: a measurement unit configured to irradiate light on an inspection object to acquire an image of the inspection object; a processing unit configured to detect an outline of the inspection object in the image of the inspection object; and an output unit configured to overlap and display the outline with reference information, wherein the processing unit is configured to determine whether the outline is good or defective based on the reference information to perform image processing on the outline according to whether the outline is good or defective.

In an embodiment, the reference information includes a reference value for determining whether at least one of a height, a width or a slope of the inspection object is good or defective.

In an embodiment, the output unit includes: a first display unit configured to overlap and display the image-processed outline with the reference information; and a second display unit configured to display the image-processed outline together with the reference value for each of the height and the width of the reference information.

In an embodiment, the reference information further includes a reference value for determining whether the slope of the inspection object is good or defective, and wherein the processing unit is configured to: set two reference points on the outline; obtain a slope of a straight line passing through the two reference points; and compare the slope of the straight line and the reference information to determine whether the inspection object is good or defective.

In an embodiment, the output unit includes: a first display unit configured to overlap and display the image-processed outline with the reference information; and a second display unit configured to display the image-processed outline together with the reference value for each of the height, the width and the slope of the reference information.

In an embodiment, the first display unit is configured to overlap and display the image-processed outline with the reference information in three dimensions, and the second display unit is configured to display the image-processed outline together with the reference value for each of the height, the width and the slope of the reference information in two dimensions.

A method of inspecting an inspection object according to another embodiment, includes: irradiating light on the inspection object to acquire an image of the inspection object; detecting an outline of the inspection object in the image of the inspection object; determining whether the outline is good or defective based on reference information to perform image processing on the outline according to whether the outline is good or defective; and overlapping and displaying the image-processed outline with the reference information.

In another embodiment, the reference information includes a reference value for determining whether at least one of a height, a width or a slope of the inspection object is good or defective.

In another embodiment, overlapping and displaying the image-processed outline with the reference information further includes displaying the image-processed outline together with the reference value for each of the height and the width of the reference information.

In another embodiment, determining whether the outline is good or defective based on reference information to perform image processing on the outline according to whether the outline is good or defective includes: setting two reference points on the outline of the inspection object; obtaining a slope of a straight line passing through the two reference points; and comparing the slope of the straight line and the reference information to determine whether the inspection object is good or defective.

In another embodiment, overlapping and displaying the image-processed outline with the reference information includes displaying the image-processed outline together with the reference value for each of the height, the width and the slope of the reference information.

The present disclosure may perform image processing on an outline of an inspection object according to whether the inspection object is good or defective and display the image-processed outline, so that a user can easily determine whether the inspection object is good or defective.

Further, the present disclosure may overlap and display an image-processed outline with reference information for determining whether an inspection object is good or defective, so that a user can easily determine what reference information is suitable for the inspection object or what reference information is not suitable for the inspection object.

DETAILED DESCRIPTION

Hereinafter, embodiments of the present disclosure will be described with reference to the accompanying drawings. In the following description, well-known functions or configurations will not be described in detail if they obscure the subject matter of the present disclosure.

First Embodiment

Figure 1:
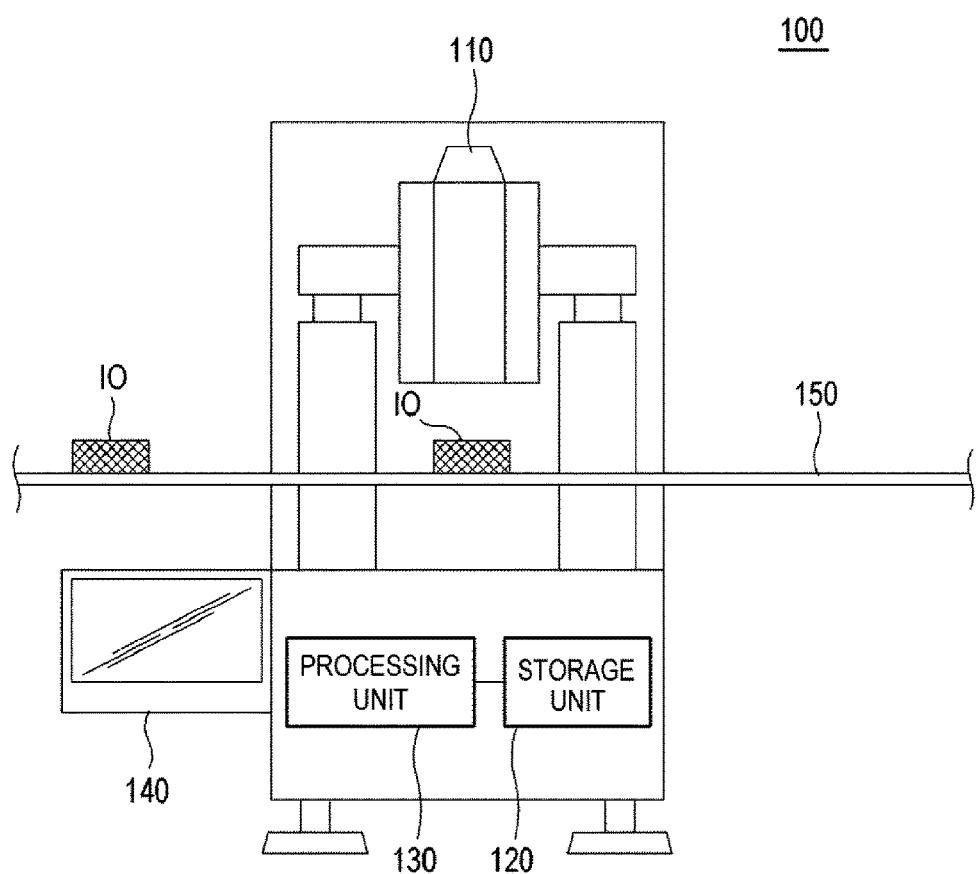
FIG. 1 is a view schematically showing an inspection system according to a first embodiment of the present disclosure.

FIG. 1 is a view schematically showing an inspection system according to a first embodiment of the present disclosure. Referring to FIG. 1, an inspection system 100 according to the present embodiment includes a data acquisition unit 110.

The data acquisition unit 110 irradiates light on an inspection object IO, and receives light reflected by the inspection object to acquire image data of the inspection object. In the present embodiment, the inspection object includes a solder joint which is a junction portion of a component of a printed circuit board and solder, but may not be limited thereto.

Figure 2:
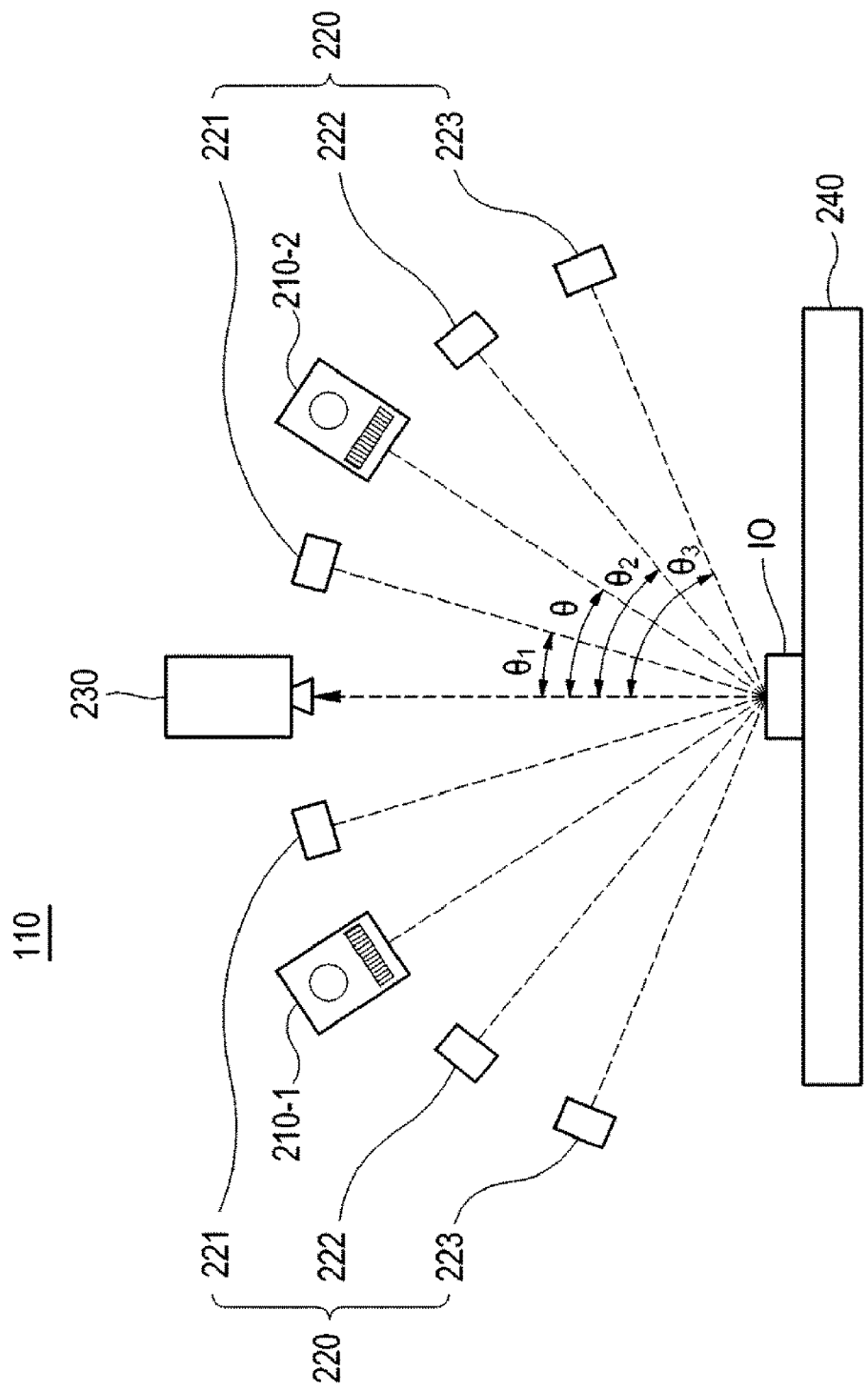
FIG. 2 is a view schematically showing the configuration of a data acquisition unit according to the first embodiment of the present disclosure.

FIG. 2 schematically shows the data acquisition unit 110 according to the first embodiment of the present disclosure. Referring to FIG. 2, the data acquisition unit 110 includes projection units 210-1 and 210-2. The projection units 210-1 and 210-2 irradiate the inspection object IO with pattern illumination for acquiring first image data of the inspection object IO. The first image data include grating pattern image data, but may not be limited thereto, and various patterns capable of measuring a sine wave can be used.

In an embodiment, the projection units 210-1 and 210-2 include a light source (not shown) for generating light, a grating element (not shown) for converting the light from the light source into pattern illumination, a grating transfer mechanism (not shown) for pitch-transferring the grating element, and a projection lens (not shown) for projecting the pattern illumination converted by the grating element onto the inspection object IO. Here, the grating element may be transferred by a predetermined distance (for example, $2\pi/N$ (N is a natural number equal to or greater than 2)) through the grating transfer mechanism such as a piezo (PZT) actuator for phase shift of the pattern illumination. Unlike this, instead of using the grating element and the grating transfer mechanism, an image of a liquid crystal display device may be used to irradiate the inspection object with phase-shifted patterned light. However, the present disclosure may not be limited thereto, and other means capable of irradiating the inspection object with the phase-shifted patterned light may be implemented.

A plurality of projection units 210-1 and 210-2 may be provided to be spaced apart from each other at a predetermined angle along the circumferential direction. The projection units 210-1 and 210-2 are provided so as to incline at a predetermined angle with respect to the inspection object IO and irradiate the inspection object IO with pattern illumination at a predetermined inclination angle θ from a plurality of directions.

The data acquisition unit 110 further includes an illumination unit 220. The illumination unit 220 irradiates the inspection object IO with at least two different colors of light to acquire second image data of the inspection object IO. The second image data include planar color image data, but may not be limited thereto.

In an embodiment, the illumination unit 220 includes a first illumination unit 221 for irradiating the inspection object IO with first color light at a first inclination angle θ1, a second illumination unit 222 for irradiating the inspection object IO with second color light at a second inclination angle θ2, and a third illumination unit 223 for irradiating the inspection object IO with third color light at a third inclination angle θ3. Here, the first inclination angle θ1 may be smaller than the inclination angle θ of the projection units 210-1 and 210-2, and each of the second inclination angle θ2 and the third inclination angle θ3 may be larger than the inclination angle θ of the projection units 210-1 and 210-2. In addition, the first to third color lights have different colors, and may have, for example, red, green, and blue colors, respectively.

In an embodiment, each of the first illumination unit 221, the second illumination unit 222, and the third illumination unit 223 may have a ring shape or a polygonal shape such as a regular hexagon, and for example, LED illumination devices may be consecutively arranged to generate ring-shaped monochrome illumination.

In an embodiment, the first inclination angle θ1 may be, for example, set to be 0° to 10° so that the first color light is irradiated almost vertically with respect to the inspection object IO. In this case, the first illumination unit 221 may be coaxial illumination with respect to an imaging unit 230, which will be described later. In addition, the first illumination unit 221 may not have a ring shape and may be disposed around the imaging unit 230 in accordance with the suitability of the mechanical arrangement design, and may adopt a mirror (not shown) or a beam splitter (not shown) for changing an optical path such that light generated by the first illumination unit 221 is irradiated vertically downward. In this case, the inclination angle of the light irradiated from the first illumination unit 221 may be set, for example, to be 85° to 95° with respect to a normal line perpendicular to the plane of the inspection object IO, and the first inclination angle θ1 of the light which is irradiated on the inspection object IO via the mirror or the beam splitter may be set, for example, to be 0° to 10° as described above.

The data acquisition unit 110 further includes the imaging unit 230. The imaging unit 230 receives light, which is irradiated from the projection units 210-1 and 210-2 and is reflected by the inspection object IO, to acquire first image data of the inspection object IO. In addition, the imaging unit 230 receives light, which is irradiated from the illumination unit 220 and is reflected by the inspection object IO, to acquire second image data of the inspection object IO. As an example, the imaging unit 230 may be provided at a vertical upper position from the inspection object IO. As another example, a plurality of imaging units 230 may be provided at the vertical upper position from the inspection object IO, may be spaced apart from each other at a predetermined angle along the circumferential direction, and may be provided at a position lower than the upper position. As yet another example, in the state in which the plurality of imaging units 230 are spaced apart from each other at the predetermined angle along the circumferential direction and is provided at the position lower than the upper position, the projection units may be provided at the vertical upper position from the inspection object IO. In this case, the plurality of imaging units may image the light, which is irradiated to the inspection IO from the projection units and is reflected by the inspection IO. Further, the imaging unit may be further provided through the beam splitter between the projection units and the inspection object IO.

The imaging unit 230 includes a charge coupled device (CCD) camera or a complementary metal oxide semiconductor (CMOS) camera, but may not necessarily be limited thereto.

The data acquisition unit 110 further includes a stage 240. The stage 240 supports and fixes the inspection object IO. In an embodiment, the stage 240 includes a first stage (not shown) configured to support and fix one end of the inspection object IO and a second stage (not shown) configured to support and fixed the other end of the inspection object IO.

Since the data acquisition unit 110 shown in FIG. 2 shows an embodiment of one of inspection apparatuses for acquiring two-dimensional or three-dimensional image data corresponding to the inspection object IO, it should be noted that the data acquisition unit 110 may not be necessarily limited to the form shown in FIG. 2.

Referring again to FIG. 1, the inspection system 100 further includes a storage unit 120. The storage unit 120 stores reference information for determining whether the inspection object IO is good (GOOD) or defective (NG). In addition, the storage unit 120 may store the image data acquired by the data acquisition unit 110.

In an embodiment, the reference information includes a reference value for determining whether a height of the inspection object IO is good or defective. As an example, the reference value for the height of the inspection object IO may include a single reference value of an upper limit or a lower limit. For example, the upper limit reference value may be a reference value for determining excess application of solder, and the lower limit reference value may be a reference value for determining insufficient application of solder. As another example, the reference value for the height of the inspection object IO may include double reference values of an upper limit and a lower limit. The reference value for the height can be variously set according to the type of the inspection object IO, inspection conditions and the like, and thus a detailed description thereof will be omitted in this embodiment.

In another embodiment, the reference information may further include a reference value for determining whether a width of the inspection object IO is good or defective. As an example, the reference value for the width of the inspection object IO includes a single reference value of an upper limit or a lower limit for each of a left side and a right side with respect to a center of the inspection object IO. For example, the upper limit reference value may be a reference value for determining excess application of solder, and the lower limit reference value may be a reference value for determining insufficient application of solder. As another example, the reference value for the width of the inspection object IO includes double reference values of an upper limit and a lower limit for each of the left side and the right side with respect to the center of the inspection object IO. The reference value for the width can be variously set according to inspection conditions of the inspection object IO, and thus a detailed description thereof will be omitted in this embodiment.

In yet another embodiment, the reference information may further include a reference value for determining whether a slope of the inspection object IO is good or defective. The reference value for the slope can be variously set according to inspection conditions of the inspection object IO, and thus a detailed description thereof will be omitted in this embodiment.

The inspection system 100 may further include a processing unit 130. The processing unit 130 generates an image of the inspection object IO based on the image data acquired by the data acquisition unit 110. Further, the processing unit 130 detects an outline of the inspection object IO in the image of the inspection object IO. In addition, the processing unit 130 determines whether the detected outline is good or defective based on the reference information stored in the storage unit 120, and performs image processing on the outline according to whether the outline is good or defective. Further, the processing unit 130 may perform image processing for visualizing the reference information using any one of dots, dashed lines, ruled lines, solid lines, faces, meshes, stereoscopic polygons, and voxels of preset colors. The operations of the processing unit 130 will be described in more detail below.

The inspection system 100 further includes an output unit 140. The output unit 140 displays the outline of the inspection object IO by overlapping the outline of the inspection object IO with the reference information. In addition, the output unit 140 may display the image of the inspection object IO generated by the processing unit 130.

In an embodiment, the output unit 140 includes a display unit (not shown) for overlapping and displaying the image-processed outline by the processing unit 130 with the reference information. The image-processed outline by the processing unit 130 may be displayed in three dimensions.

In another embodiment, the output unit 140 includes a first display unit ($DP_1$; see FIG. 12) for overlapping and displaying the image-processed outline by the processing unit 130 with the reference information, and a second display unit ($DP_2$; see FIG. 12) for displaying the image-processed outline by the processing unit 130 together with the reference value for each of the height and the width of the reference information. The image-processed outline may be displayed in two dimensions or three dimensions. Further, in the case of the first display unit $DP_1$, the reference information displayed to be overlapped with the image-processed outline may be displayed together with the reference values for the height and the width.

In yet another embodiment, the output unit 140 includes the first display unit $DP_1$ for overlapping and displaying the image-processed outline by the processing unit 130 with the reference information, and the second display unit $DP_2$ for displaying the image-processed outline by the processing unit 130 together with the reference value for each of the height, the width, and the slope of the reference information. The image-processed outline may be displayed in two dimensions or three dimensions. In the case of the first display unit $DP_1$, the reference information displayed to be overlapped with the image-processed outline may be displayed simultaneously with the reference values for the height, the width, and the slope.

The inspection system 100 further includes a transfer unit 150. The transfer unit 150 transfers the inspection object IO to the data acquisition unit 110 so that the data acquisition unit 110 may acquire image data of the inspection object IO. The transfer unit 150 includes a conveyor (not shown) and the like, but may not be limited thereto.

Hereinafter, the operations of the processing unit 130 according to the present embodiment will be described in detail with reference to FIGS. 3 to 12. In the present embodiment, for convenience of explanation, it is assumed that the inspection object IO is solder applied to a component of a printed circuit board.

Figure 3:
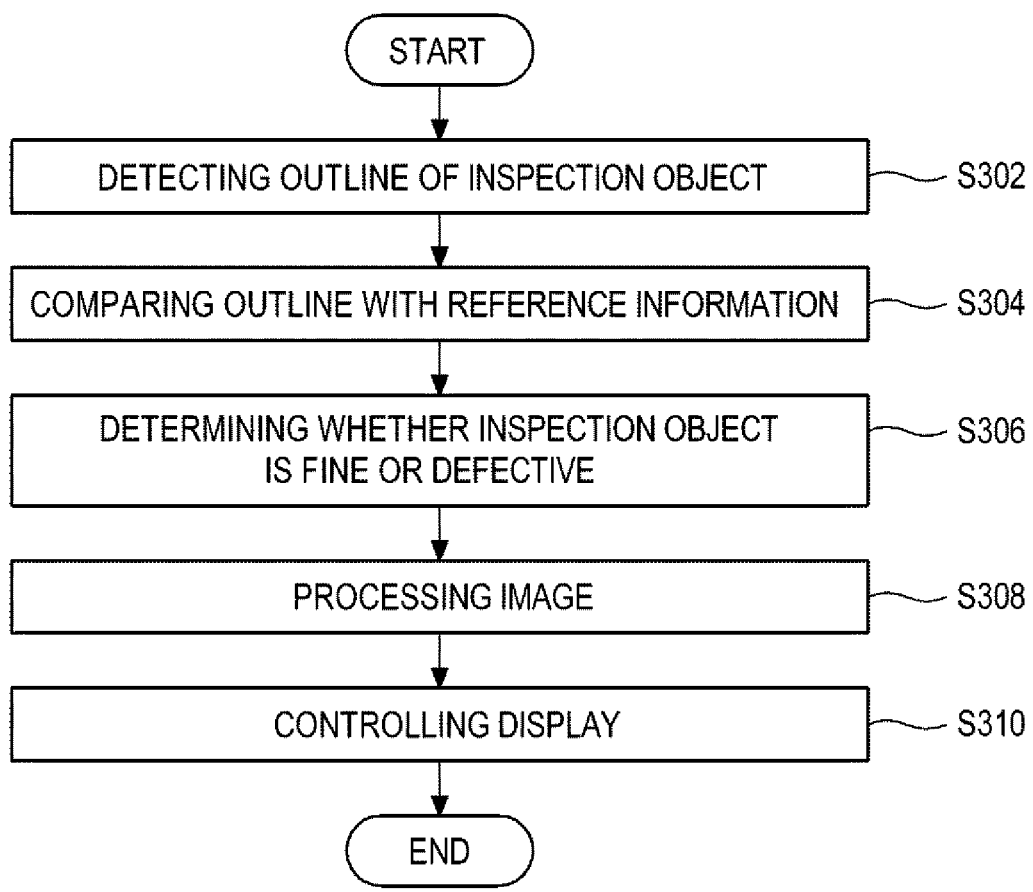
FIG. 3 is a flowchart showing procedures for determining whether an inspection object is good or defective based on reference information to perform image processing according to the first embodiment of the present disclosure.

FIG. 3 is a flowchart showing procedures for determining whether the inspection object IO is good or defective based on reference information to perform image processing according to an embodiment of the present embodiment. Referring to FIG. 3, the processing unit 130 detects an outline of the inspection object IO based on image data of the inspection object IO (S302).

In an embodiment, the processing unit 130 generates a first image based on first image data acquired by the imaging unit 110, and acquires brightness information from the first image. In addition, the processing unit 130 generates a second image based on second image data acquired by the imaging unit 110, and acquires color information from the second image. At this time, the first image and the second image may be synthesized to generate a composite image, and the brightness information and the color information may be acquired from the composite image. Next, the processing unit 130 sets an inspection region on the composite image of the first image and the second image, and detects a change in a pixel value within the set inspection region. That is, the processing unit 130 sets a section within the set inspection region where the color of pixels changes from a first color to a second color. Next, the processing unit 130 detects a change in color per pixel and a change in brightness per pixel in the set region. Next, the processing unit 130 detects the outline of the inspection object IO based on the change in color per pixel and the change in brightness per pixel.

At this time, the processing unit 130 may store design information (for example, CAD) of the inspection object IO and may detect the outline of the inspection object IO by comparing three-dimensional shape information acquired by the data acquisition unit 110 and the design information.

In the above-described embodiment, an example where the outline of the inspection object IO is detected based on the change in color per pixel and the change in brightness per pixel in the image corresponding to the inspection object IO has been described, but it should be noted that the example may not necessarily be limited to the above-described method since the example represents any one of the embodiments capable of detecting the outline of the inspection object IO.

Referring back to FIG. 3, the processing unit 130 compares the detected outline and the reference information stored in the storage unit 120 (S304), and determines whether the outline of the inspection object IO is good or defective (S306).

Figure 4:
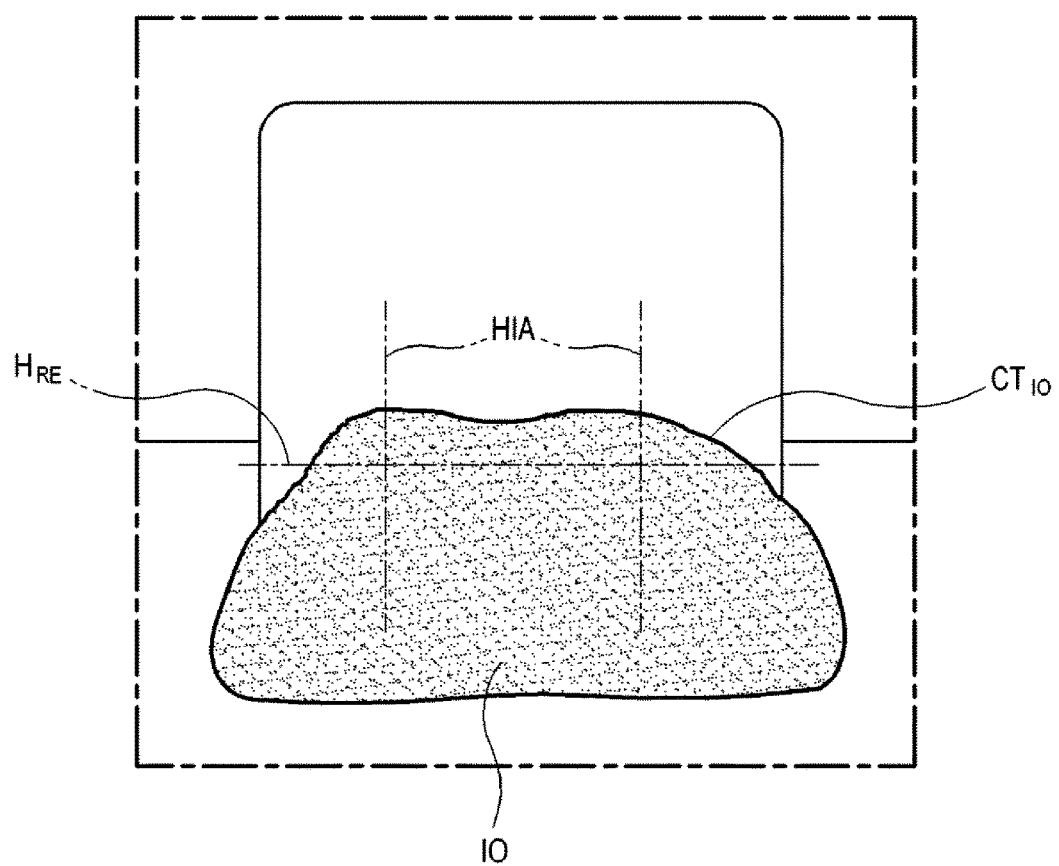
FIG. 4 shows an example of determining whether a height of an outline is good or defective according to the first embodiment of the present disclosure.

In an embodiment, as shown in FIG. 4, the processing unit 130 sets a height inspection region (HIA) having a predetermined size with respect to a center of the inspection object IO, based on the detected outline $CT_{IO}$. The processing unit 130 compares a height of the outline $CT_{IO}$ of the inspection object IO with a reference value $H_{RE}$ for the height of the reference information within the height inspection region (HIA), and determines whether the height of the inspection object IO is good or defective, that is, whether the height of the outline $CT_{IO}$ of the inspection object IO is good or defective. In FIG. 4, although the reference value $H_{RE}$ for the height is shown as a single reference value, it may not be necessarily limited thereto and may be double reference values of upper and lower limits.

Figure 5:
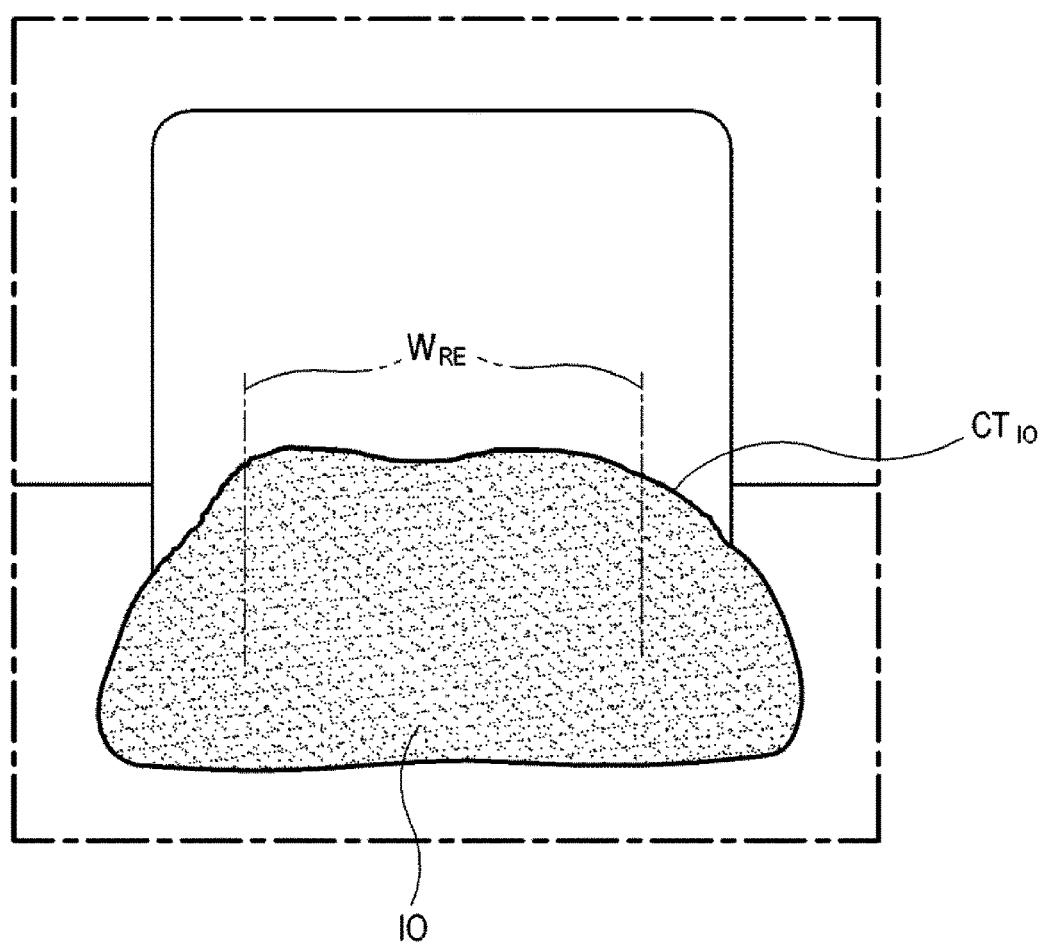
FIG. 5 shows an example of determining whether a width of an outline is good or defective according to the first embodiment of the present disclosure.

In addition, as shown in FIG. 5, the processing unit 130 detects a width of the outline $CT_{IO}$ of the inspection object IO, and compares the detected width of the outline $CT_{IO}$ of the inspection object IO with a reference value $W_{RE}$ for the width of the reference information to determine whether the width of the inspection object IO is good or defective, that is, whether the width of the outline $CT_{IO}$ of the inspection object IO is good or defective. In FIG. 5, although the reference value $W_{RE}$ for the width is shown as a single reference value for each of the left side and the right side with respect to a center of the inspection object IO, it may not be limited thereto and may be double reference values of the upper limit and the lower limit for each of the left side and the right side with respect to the center of the inspection object IO.

Figure 6:
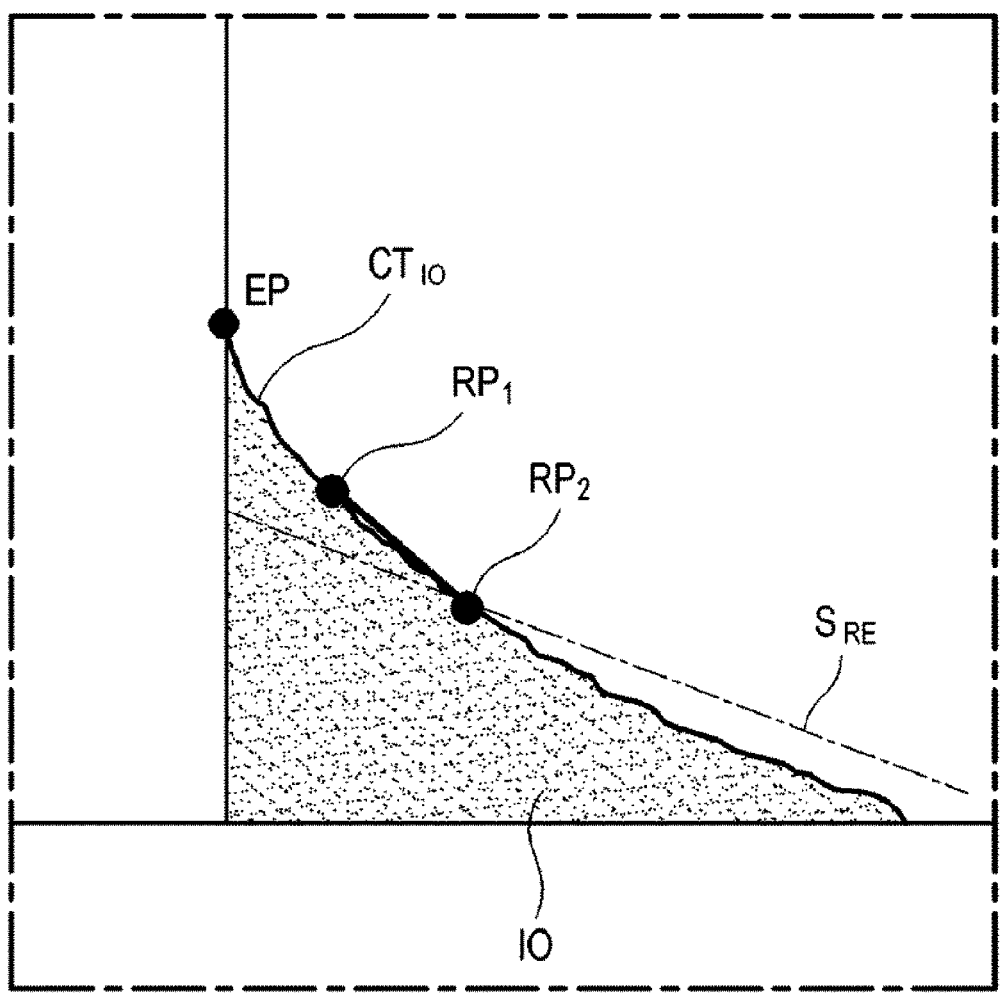
FIG. 6 shows an example of determining whether a slope of an outline is good or defective according to the first embodiment of the present disclosure.

In addition, the processing unit 130 sets at least one reference point in the outline $CT_{IO}$ of the inspection object IO, and calculates a slope with respect to the set reference point. As an example, as shown in FIG. 6, the processing unit 130 sets a first reference point $RP_1$ at a position spaced by a first distance with respect to an end point EP of the outline $CT_{IO}$ of the inspection object IO, and sets a second reference point $RP_2$ at a position spaced by a second distance with respect to the end point EP of the outline $CT_{IO}$ of the inspection object IO. The first distance is shorter than the second distance. The processing unit 130 calculates a slope of a straight line passing through the first reference point $RP_1$ and the second reference point $RP_2$. As another example, the processing unit 130 sets one reference point at a position spaced by a predetermined distance with respect to the end point EP of the outline $CT_{IO}$ of the inspection object IO, and calculates an instantaneous slope (inclination) with respect to the set reference point. The processing unit 130 compares the calculated slope with a reference value $S_{RE}$ for the slope of the reference information, and determines whether the slope of the inspection object IO is good or defective, that is, whether the slope of the outline $CT_{IO}$ of the inspection object IO is good or defective.

Referring back to FIG. 3, the processing unit 130 performs image processing on the outline $CT_{IO}$ of the inspection object IO according to whether the inspection object IO is good or defective (S308). In an embodiment, the processing unit 130 performs image processing for visualizing the outline $CT_{IO}$ of the inspection object IO using any one of dots, dashed lines, ruled lines, solid lines, faces, meshes, stereoscopic polygons and voxels of preset colors according to whether the inspection object IO is good or defective.

Figure 7:
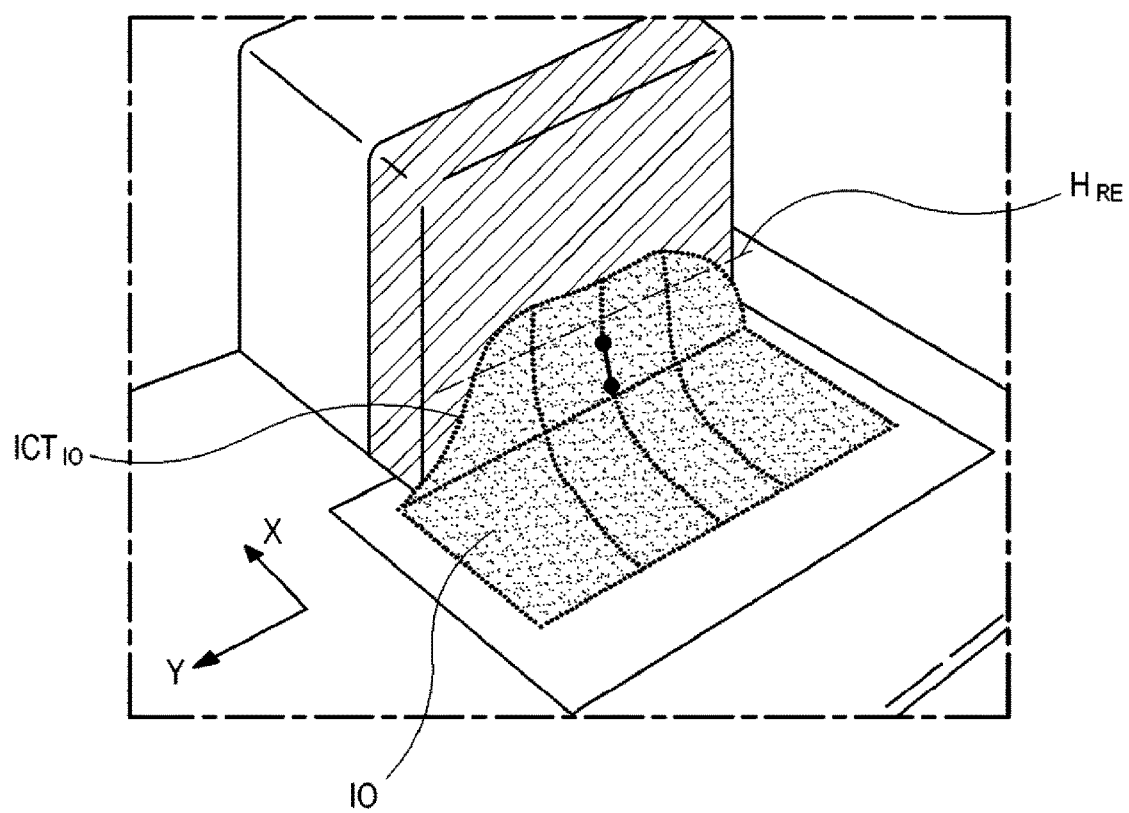
FIG. 7 shows an example of displaying an image-processed outline and reference information according to the first embodiment of the present disclosure.

As an example, if it is determined that each of the height, the width and the slope of the inspection object IO is good (GOOD), the processing unit 130 performs image processing indicative of "good" on the outline $CT_{IO}$ of the inspection object IO, thereby generating an image-processed outline $ICT_{IO}$ as shown in FIG. 7. In FIG. 7, the image-processed outline $ICT_{IO}$ is indicated by a black dashed line, but it may be indicated by a blue dashed line. In FIG. 7, a reference numeral $H_{RE}$ represents a reference value for the height. In FIG. 7, although the reference value for the height $H_{RE}$ is shown as the reference information, it may not be limited thereto and a reference value for each of the width and the slope may be further shown.

Figure 8:
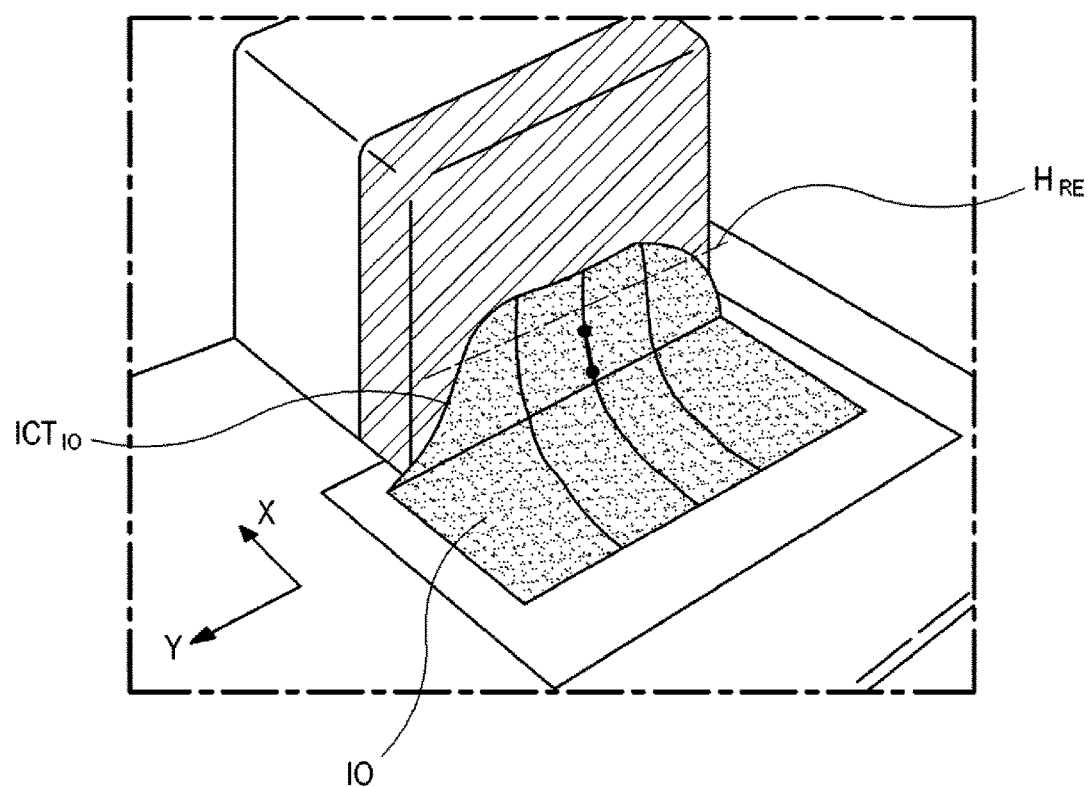
FIG. 8 shows another example of displaying an image-processed outline and reference information according to the first embodiment of the present disclosure.

As another example, if it is determined that each of the height, the width and the slope of the inspection object IO is good (GOOD), the processing unit 130 performs image processing indicative of "good" on the outline $CT_{IO}$ of the inspection object IO, thereby generating an image-processed outline $ICT_{IO}$ as shown in FIG. 8. In FIG. 8, the image-processed outline $ICT_{IO}$ is indicated by a black solid line, but it may be indicated by a blue solid line. In FIG. 8, the reference numeral $H_{RE}$ represents the reference value for the height. In FIG. 8, although the reference value for the height $H_{RE}$ is shown as the reference information, it may not be limited thereto and a reference value for each of the width and the slope may be further shown.

Figure 9:
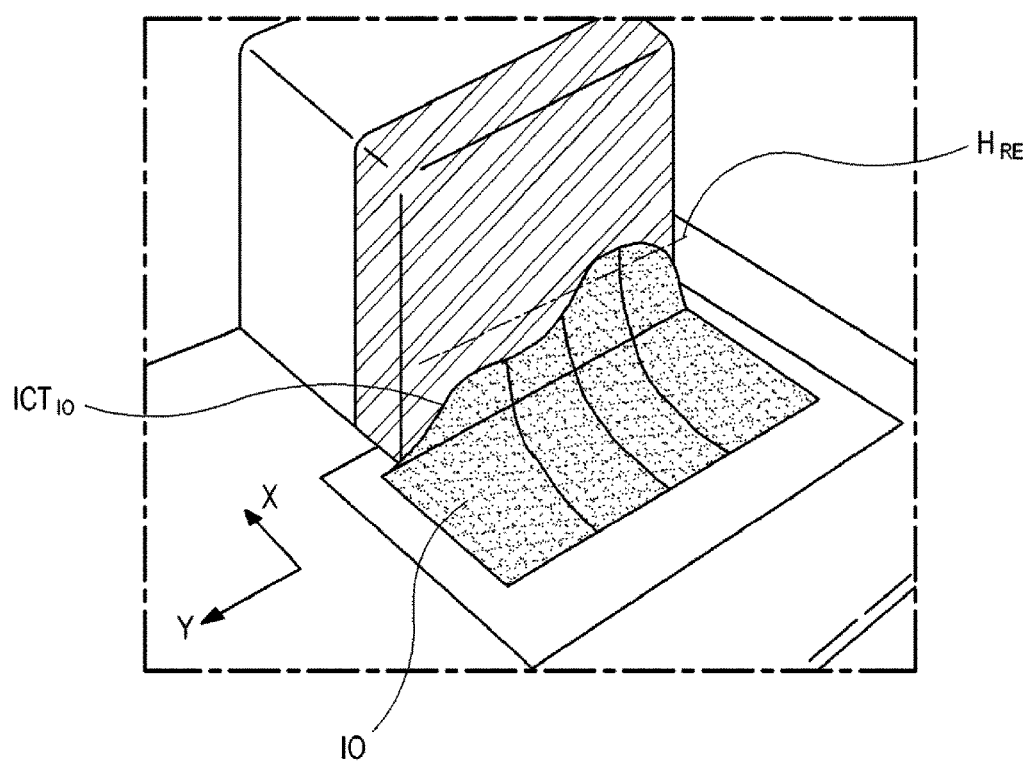
FIG. 9 shows yet another example of displaying an image-processed outline and reference information according to the first embodiment of the present disclosure.

As still another example, if it is determined that the height of the inspection object IO is defective (NG) and each of the width and the slope of the inspection object IO is good (GOOD), the processing unit 130 performs image processing indicative of "defective" on the outline $CT_{IO}$ of the inspection object IO, thereby generating an image-processed outline $ICT_{IO}$ as shown in FIG. 9. In FIG. 9, the image-processed outline $ICT_{IO}$ is indicated by a black solid line, but it may be indicated by a red solid line. In FIG. 9, the reference numeral $H_{RE}$ represents the reference value for the height. In FIG. 9, although the reference value for the height $H_{RE}$ is shown as the reference information, it may not be limited thereto and a reference value for each of the width and the slope may be further shown.

Figure 10:
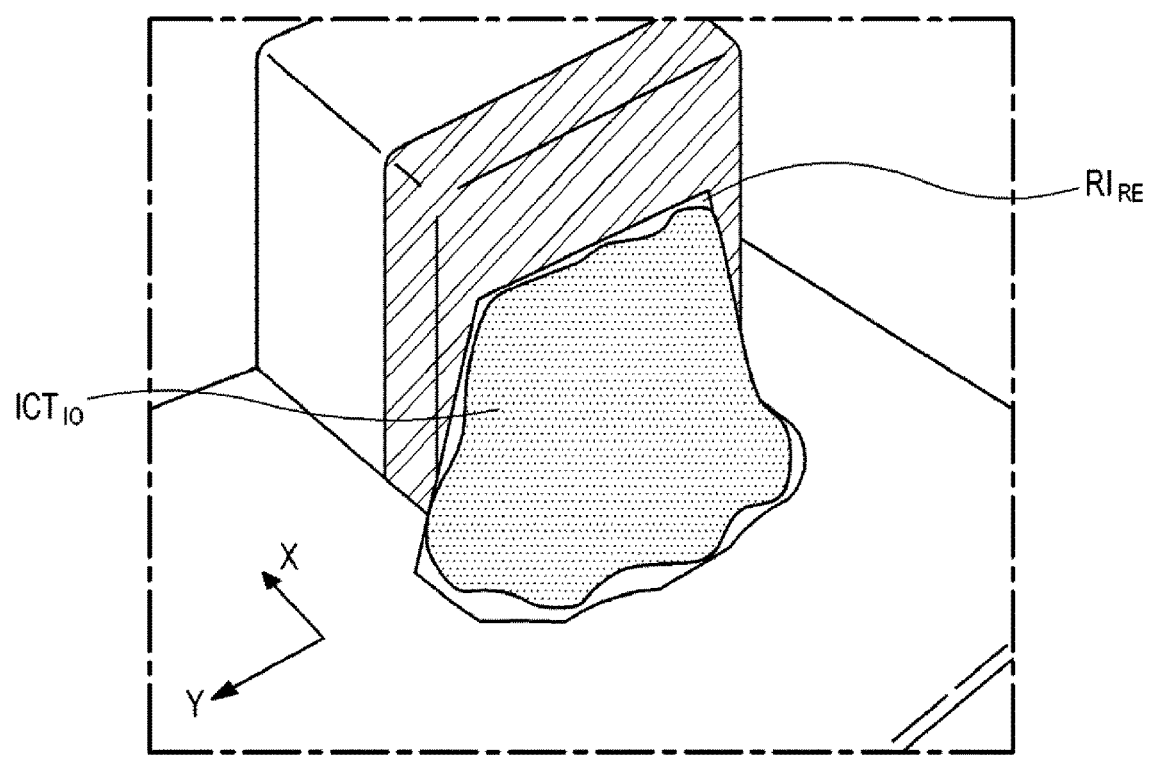
FIG. 10 shows still another example of displaying an image-processed outline and reference information according to the first embodiment of the present disclosure.

As yet another example, if it is determined that each of the height, the width and the slope of the inspection object IO is good (GOOD), the processing unit 130 performs image processing indicative of "good" on the outline $CT_{IO}$ of the inspection object IO, thereby generating an image-processed outline $ICT_{IO}$ as shown in FIG. 10. In FIG. 10, the image-processed outline $ICT_{IO}$ is displayed as a shaded three-dimensional shape, but it can be displayed as a blue three-dimensional shape. In FIG. 10, a reference numeral $RI_{RE}$ represents reference information, which may be displayed as a green three-dimensional shape.

Figure 11:
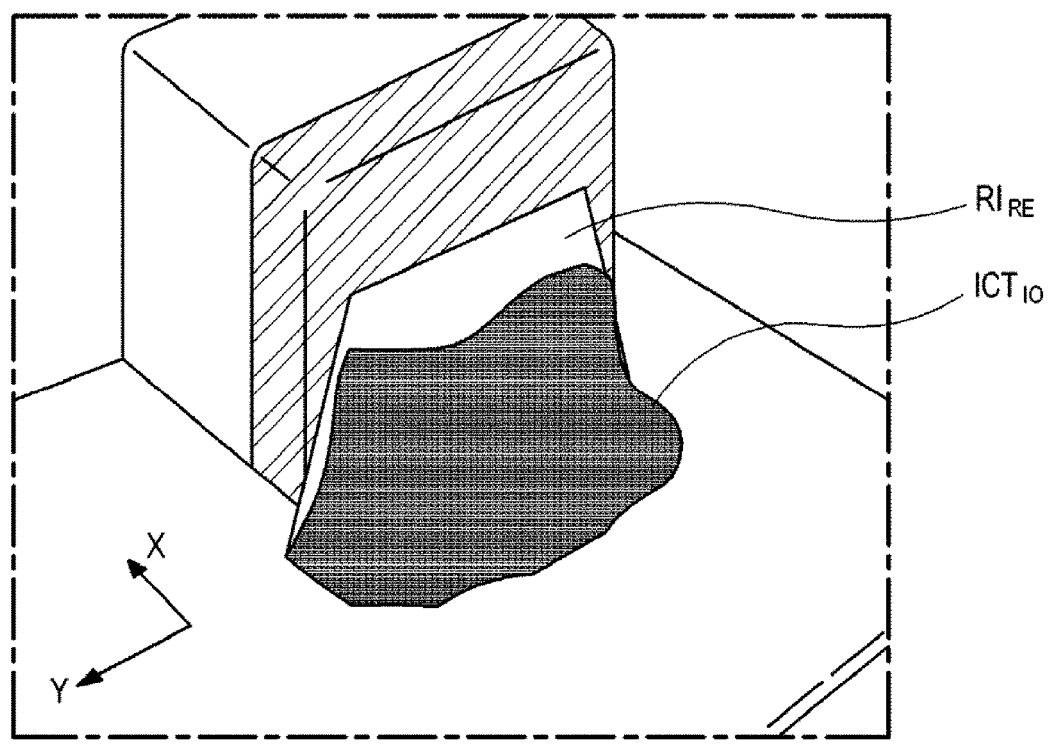
FIG. 11 shows a further example of displaying an image-processed outline and reference information according to the first embodiment of the present disclosure.

As a further example, if it is determined that the height of the inspection object IO is defective (NG) and each of the width and the slope of the inspection object IO is good (GOOD), the processing unit 130 performs image processing indicative of "defective" on the outline $CT_{IO}$ of the inspection object IO, thereby generating an image-processed outline $ICT_{IO}$ as shown in FIG. 11. The image-processed outline $ICT_{IO}$ in this example is displayed as a shaded three-dimensional shape, but it can be displayed as a red three-dimensional shape. In FIG. 11, the reference numeral $RI_{RE}$ represents reference information, which may be displayed as a green three-dimensional shape.

Figure 12:
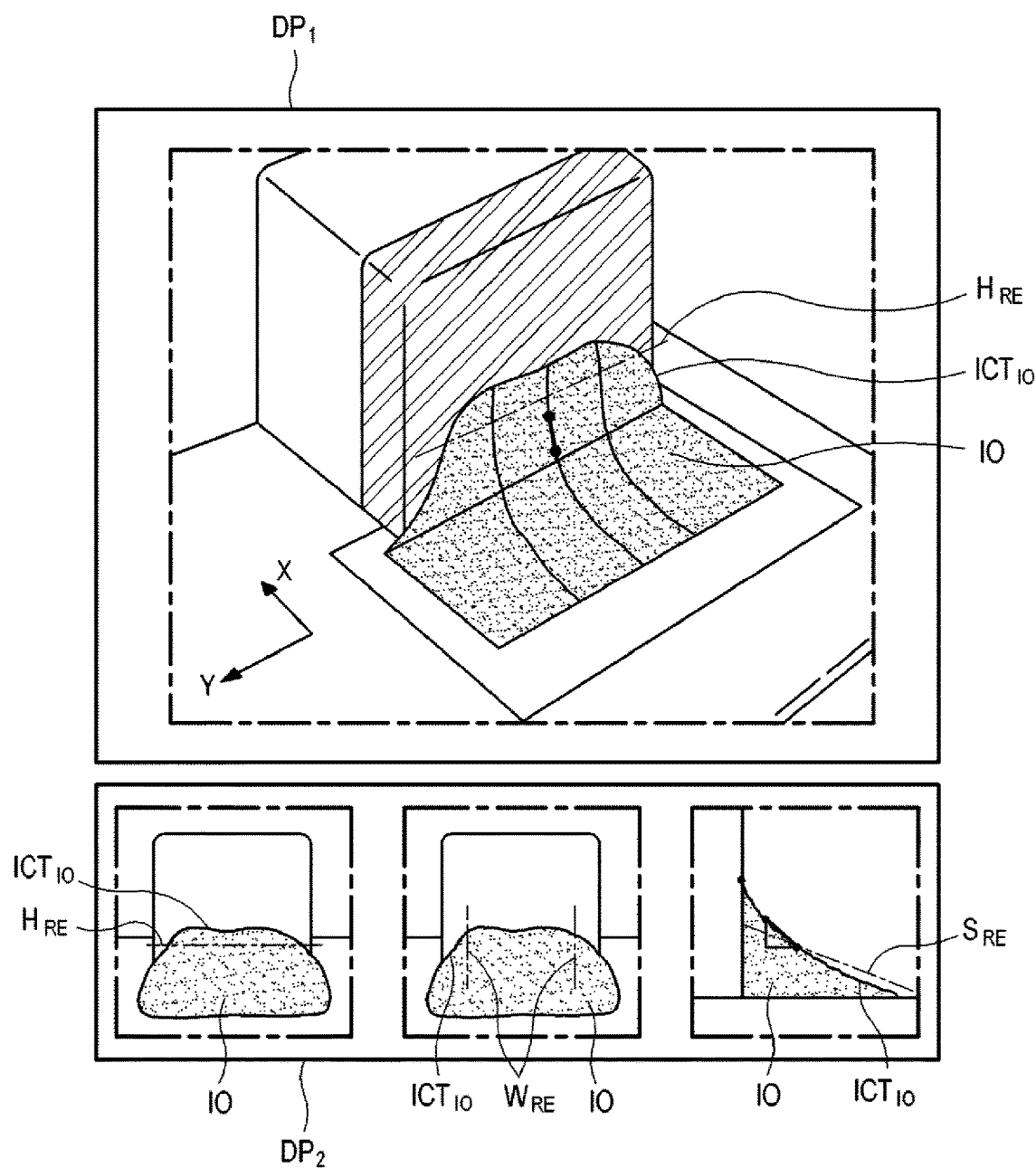
FIG. 12 shows a further example of displaying an image-processed outline and reference information according to the first embodiment of the present disclosure.

Referring back to FIG. 3, the processing unit 130 controls display of the image-processed outline and the reference information (S310). In an embodiment, the processing unit 130 controls the image-processed outline $ICT_{IO}$ to be overlapped with the reference information and displayed on the output unit 140 as shown in FIGS. 7 to 11. In another embodiment, as shown in FIG. 12, the processing unit 130 controls the image-processed outline $ICT_{IO}$ to be overlapped with the reference information and displayed on the first display unit $DP_1$ of the output unit 140, and controls the image-processed outline $ICT_{IO}$ to be displayed on the second display unit $DP_2$ of the output unit 140 together with the reference value for each of the height, the width, and the slope of the reference information.

Second Embodiment

Figure 13:
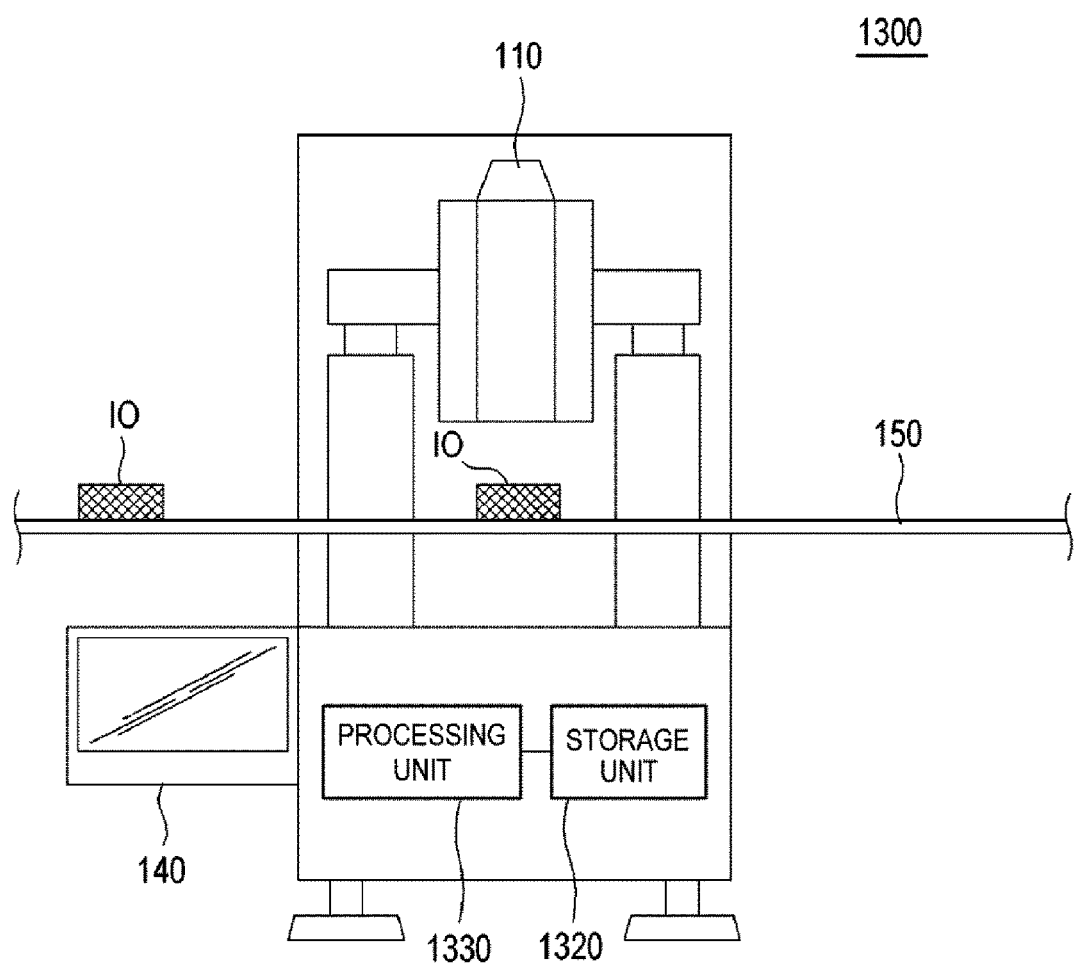
FIG. 13 is a view schematically showing an inspection system according to a second embodiment of the present disclosure.

FIG. 13 is a block diagram schematically showing the configuration of an inspection system 1300 according to a second embodiment of the present disclosure. In this embodiment, the same components as those of the first embodiment are denoted by the same reference numerals and description thereof will be omitted.

Referring to FIG. 13, the inspection system 1300 includes a storage unit 1320. The storage unit 1320 stores reference information for determining whether an inspection object is good or defective. In the present embodiment, the inspection object includes a rear case for a mobile phone made of plastic or metal, but may not be limited thereto. In addition, the storage unit 1320 may store image data of the inspection object acquired by the data acquisition unit 110.

In an embodiment, the reference information includes a reference value for determining whether each of a height, a width, and a slope of the inspection object IO is good or defective. The reference value for each of the height, the width, and the slope may be variously set according to the type of the inspection object IO, inspection conditions, and the like, and thus a detailed description thereof will be omitted in this embodiment.

In another embodiment, the reference information may further include a reference value for determining whether an outer appearance of the inspection object IO is good or defective. The reference value for the outer appearance may be a reference value for scratches, dent, color deviations, cutting dimensions, perforations or the like, but may not be limited thereto. In addition, the reference value for the outer appearance can be variously set according to the type of the inspection object IO, inspection conditions and the like, and thus a detailed description thereof will be omitted in this embodiment.

In yet another embodiment, the reference information may further include three-dimensional reference data of the inspection object IO. The three-dimensional reference data include three-dimensional design data (e.g., CAD) or previously imaged three-dimensional shape data, but may not necessarily be limited thereto. The three-dimensional reference data may be variously set according to the type of the inspection object IO, inspection conditions and the like, and thus a detailed description thereof will be omitted in this embodiment.

The inspection system 1300 further includes a processing unit 1330. The processing unit 1330 detects an outline of the inspection object IO in an image of the inspection object IO acquired by the measurement unit 110. In addition, the processing unit 1330 determines whether the detected outline is good or defective based on the reference information stored in the storage unit 1320, and performs image processing on the outline according to whether the detected outline is good or defective.

In an embodiment, the processing unit 1330 determines whether each of a height, a width and a slope of the inspection object IO is good or defective based on the reference information stored in the storage unit 1320, and performs image processing on the outline of the inspection object IO. The image processing on the outline in the present embodiment is the same as or similar to the image processing on the outline in the first embodiment, and thus a detailed description thereof will be omitted in this embodiment.

In another embodiment, the processing unit 1330 sets an inspection region on the outline of the inspection object IO. Meanwhile, the processing unit 1330 may set a masking region within the set inspection region. The masking region indicates a region in which inspection of whether the outline of the inspection object IO is good or defective is not performed. The processing unit 1330 compares the reference information stored in the storage unit 1320 with the outline of the inspection object IO with respect to the inspection region, and determines whether the inspection object IO is good or defective to perform image processing on the outline of the inspection object IO according to whether the inspection object IO is good or defective. As an example, if it is determined that the outline of the inspection object IO is good (GOOD), the processing unit 1330 may perform image processing for visualizing the outline of the inspection object IO using any one of dots, dashed lines, solid lines, faces, meshes, stereoscopic polygons, and voxels of a preset color (e.g., blue). As another example, if it is determined that the outline of the inspection object IO is defective (NG), the processing unit 1330 may perform image processing for visualizing the outline of the inspection object IO using any one of dots, dashed lines, solid lines, faces, meshes, stereoscopic polygons, and voxels of a preset color (e.g., red). The processing unit 1330 controls the image-processed outline and the reference information to be overlapped with each other and displayed on the output unit 140. The image processing on the outline in this embodiment is the same as or similar to the image processing on the outline in the first embodiment, and thus a detailed description thereof is omitted in this embodiment.

While the present disclosure has been particularly shown and described with reference to preferred embodiments thereof, it will be understood by those skilled in the art that various changes and modifications may be made without departing from the spirit and scope of the appended claims.

What is claimed is:

1. An inspection system comprising:
    a measurement unit configured to irradiate light on an inspection object to acquire an image of the inspection object;
    a processing unit configured to detect an outline of the inspection object in the image of the inspection object; and
    an output unit configured to overlap and display the outline with reference information,
    wherein the processing unit is configured to:
    set a height inspection region based on a center of the outline;
    determine whether a height of the outline is good or defective based on the reference information within the height inspection region;
    set at least one reference point on the outline based on an end point of the outline;
    calculate a slope of the at least one reference point;
    determine whether the slope of the outline is good or defective based on the reference information; and
    perform image processing for visualizing the outline using any one of dots, dashed lines, solid lines, faces or three-dimensional shapes on the outline according to whether the height and the slope of the outline is good or defective.

2. The inspection system of claim 1, wherein the reference information comprises a reference value for determining whether at least one of a height, a width or a slope of the inspection object is good or defective.

3. The inspection system of claim 2, wherein the output unit comprises:
    a first display unit configured to overlap and display the image-processed outline with the reference information; and
    a second display unit configured to display the image-processed outline together with the reference value for each of the height and the width of the reference information.

4. The inspection system of claim 2,
    wherein the processing unit is configured to:
    set two reference points on the outline;
    obtain a slope of a straight line passing through the two reference points; and
    compare the slope of the straight line and the reference information to determine whether the inspection object is good or defective.

5. The inspection system of claim 4, wherein the output unit comprises:
    a first display unit configured to overlap and display the image-processed outline with the reference information; and
    a second display unit configured to display the image-processed outline together with the reference value for each of the height, the width and the slope of the reference information.

6. The inspection system of claim 5, wherein the first display unit is configured to overlap and display the image-processed outline with the reference information in three dimensions, and
    wherein the second display unit is configured to display the image-processed outline together with the reference value for each of the height, the width and the slope of the reference information in two dimensions.

7. A method of inspecting an inspection object, the method comprising:
    irradiating light on the inspection object to acquire an image of the inspection object;
    detecting an outline of the inspection object in the image of the inspection object;
    determining whether the outline is good or defective based on reference information;
    performing image processing for visualizing the outline using any one of dots, dashed lines, solid lines, faces or three-dimensional shapes on the outline according to whether the outline is good or defective; and
    overlapping and displaying the image-processed outline with the reference information, and
    wherein determining whether the outline is good or defective comprises:

setting a height inspection region based on a center of the outline;

determining whether a height of the outline is good or defective based on the reference information within the height inspection region;

setting at least one reference point on the outline based on an end point of the outline;

calculating a slope of the at least one reference point; and determining whether the slope of the outline is good or defective based on the reference information.

8. The method of claim 7, wherein the reference information comprises a reference value for determining whether at least one of a height, a width or a slope of the inspection object is good or defective.

9. The method of claim 8, wherein overlapping and displaying the image-processed outline with the reference information further comprises displaying the image-processed outline together with the reference value for each of the height and the width of the reference information.

10. The method of claim 9, wherein determining whether the outline is good or defective based on reference information to perform image processing on the outline according to whether the outline is good or defective comprises:

setting two reference points on the outline of the inspection object;

obtaining a slope of a straight line passing through the two reference points; and comparing the slope of the straight line and the reference information to determine whether the inspection object is good or defective.

11. The method of claim 10, wherein overlapping and displaying the image-processed outline with the reference information comprises displaying the image-processed outline together with the reference value for each of the height, the width and the slope of the reference information.

* * * * *